United States Patent [19]

Huber et al.

[11] Patent Number: 5,521,305
[45] Date of Patent: May 28, 1996

[54] RECYCLING MATERIALS COMPRISING CELLULOSIC AND SYNTHETIC FIBERS

[75] Inventors: Bernd Huber; Gerhard Stein, both of Kelheim, Germany

[73] Assignee: Hoechst Aktiengesellschaft, Frankfurt am Main

[21] Appl. No.: 314,791

[22] Filed: Sep. 29, 1994

[30] Foreign Application Priority Data

Oct. 1, 1993 [DE] Germany ............................ 43 33 547.0

[51] Int. Cl.$^6$ ............................ D01F 13/04; A62D 3/00; C12P 1/00; C12P 5/02
[52] U.S. Cl. ............................ 536/127; 536/128; 127/1; 127/36
[58] Field of Search .................................... 536/127, 128; 127/1, 36

[56] References Cited

U.S. PATENT DOCUMENTS

| 3,711,392 | 1/1973 | Metzger | 204/180 P |
|---|---|---|---|
| 3,937,675 | 2/1976 | Gruntfest et al. | 524/35 |
| 4,597,872 | 7/1986 | Andersson | 210/605 |
| 4,933,283 | 6/1990 | Chen et al. | 435/166 |
| 5,295,985 | 3/1994 | Romesser et al. | 604/358 |

FOREIGN PATENT DOCUMENTS

| 0133846 | 7/1984 | European Pat. Off. |
| 0154713 | 11/1980 | Germany |

OTHER PUBLICATIONS

European Search Report, No. 94114771.2, Feb. 3, 1995.

Primary Examiner—Nathan M. Nutter
Attorney, Agent, or Firm—Connolly and Hutz

[57] ABSTRACT

Recycling materials comprising cellulosic and synthetic fibers

Described is a process for recycling materials comprising fiber mixtures comprising cellulose fibers, comprising the steps of:

i) providing fiber mixtures comprising cellulosic fibers and fibers composed of synthetic polymers, and ii) subjecting these mixtures to a microbial hydrolysis in which the cellulosic fibers are completely degraded.

The process makes it possible in particular to separate fiber mixtures. For this, the microorganisms and the hydrolyzate are removed in a conventional manner following step ii), and the remaining synthetic polymers are carried off in a conventional manner to be further recycled.

3 Claims, No Drawings

RECYCLING MATERIALS COMPRISING CELLULOSIC AND SYNTHETIC FIBERS

The invention relates to a process for recycling materials comprising mixtures of cellulosic fibers and fibers composed of synthetic polymers.

To avoid increasing quantities of waste and to make better use of the Earth's resources, there is an ever increasing need for the recycling of fiber materials, including in the textile sector.

True, a form of recovery by pulling fiber materials and substantial conversion into individual fibers in the form of shoddy has long been known and practiced, but it generally leads only to articles of modest or inferior quality.

Recycling processes in which the chains of synthetic polymers are split into the monomers and are then available for a fresh synthesis avoid these disadvantages and lead to high quality products.

Such processes have been developed for example for polyester fibers, as described for example in DE-A-2,506,259, and are used. However, they can only be practiced in the case of single-material wastes.

Large amounts of synthetic fibers, especially polyester fibers, are processed in mixtures together with cellulosic fibers, such as cotton, viscose fibers or recently developed cellulosic fibers which are spun from solution, e.g., TENCEL®.

A chemical separation of cellulosic fibers using strong acids as solvents is possible, but requires the use of a large amount of chemicals and is harmful to the environment.

It is also known to subject biowastes, such as domestic waste or other compostable wastes, to a microbial hydrolysis and to further recycle the hydralyzate, for example by anaerobic fermentation.

With this approach it is possible to achieve hydrolysis of the bulk, for example 65–75%, of the biogenic organic substances and to convert the hydrolyzate into gaseous and combustible constituents consisting chiefly of methane (known as biogas).

For regenerated cellulose fiber it is known that the process of hydrolyric degradation proceeds more rapidly and to grater completion than for native cellulose (cf. I. Schnurz; A. Hönel: Enzymatische Hydrolyse von regenerierten Cellulosefasern mit Cellulose aus Trichoderma; Cellulose Chemistry And Technology, 23, 466–476 (1989)).

The workup of mixtures of cellulose fibers and synthetic fibers has not been described.

It is an object of the present invention to provide a simple process for separating and recycling fiber mixtures comprising cellulosic fibers and fibers composed of synthetic polymers.

It has been found that the hydrolyric degradation of cellulosic fibers is advantageously suitable for separating and working up fiber mixtures of cellulosic and synthetic fibers. The cellulosic fibers are completely degraded and the synthetic fiber material can be recycled in a conventional manner after the microorganisms have been removed, for example via a wash with water. The energy content of the hydrolyzate can advantageously be converted into biogas via an anaerobic fermentation.

The invention accordingly provides a process for recycling materials comprising fiber mixtures comprising cellulose fibers, comprising the steps of:

i) providing fiber mixtures comprising cellulosic fibers and fibers composed of synthetic polymers, and ii) subjecting these mixtures to a microbial hydrolysis in which the cellulosic fibers are completely degraded.

In a particularly preferred embodiment, the process is also suitable for separating mixtures of synthetic fibers and cellulosic fibers.

This embodiment of the process according to the invention further comprises, after step ii), removing the microorganisms and the hydrolyzate in a conventional manner, for example via a wash with water, and carrying off the remaining synthetic polymers in a conventional manner to be further recycled, whether by incineration or by re-use or by splitting into monomers.

In a preferred embodiment of the process according to the invention, the mixtures used comprise a) fiber mixtures comprising cellulosic fibers and fibers composed of synthetic polymers and b) further microbially hydrolyzable constituents.

As regards the polymer type of the fibers composed of synthetic polymers, the process of the invention is not subject to any restrictions.

The materials to be recycled can be in the form of yarns or else in the form of textile sheet materials, such as knitted fabrics, woven fabrics, nonwoven fabrics or felts. As regards the linear density and the fiber length, the process of the invention is not subject to any restrictions. It is possible to use materials comprising staple fibers or else continuous filaments.

Preferred substrates for cellulosic fibers include for example cotton, viscose, modal, and cellulosic fibers spun from solvents.

Preferred substrates for fibers composed of synthetic polymers include for example polyesters, for example polyethylene or polybutylene terephthalates, polyamides, such as Perlon or nylon grades, polyolefins, for example polypropylene or polyethylene, or aramids.

The process of the invention can be carried out in industrial plants for the processing of biowaste, such as garden waste or kitchen waste. For industrial practice in these plants, which are optimized for biowaste, it is advantageous to carry out a preliminary comminution by cutting or pulling yarns or sheetlike structures composed of fiber mixtures in order that the conveying of the suspension in the form of an aqueous slurry may be ensured.

The process of the invention can be carried out in aqueous suspension in the presence of biowaste suspensions or in pure form. If fiber mixtures only are used, it is advisable to add the trace elements required for the growth of the hydrolase-producing bacteria.

In order that, following the hydrolysis of the cellulosic fibers, the purification of the left-behind fibers composed of synthetic polymers may be facilitated, it is advantageous to restrict the proportion of biowaste suspension to the minimum content required for the process, or to dispense with it completely.

Very particular preference is given to following the microbial hydrolysis with an anaerobic fermentation in which the hydrolyzate is completely fermented to biogas. The anaerobic fermentation of the hydrolyzate can also be carried out in one step with the microbial hydrolysis.

The Example which follows describes the invention without limiting it.

EXAMPLE 1

Hydrolysis of a polyester-viscose fiber mixture.

A 65/35% polyester-viscose blend yarn was subjected to a combined hydrolysis and fermentation test. The blend yarn was fed together with a biowaste suspension formed from garden waste and wet biowaste from an industrial plant for biowaste processing (containing 10 g of organic dry matter). The batches were hydrolyzed and directly anaerobically fermented in a one-stage process.

For the hydrolysis, 100 ml of the biowaste suspension were admixed with 3.5 g of a polyester-viscose blend yarn containing 65% of polyester fibers having a linear density of 1.7 dtex and 35% of a viscose fiber having a linear density of 1.3 dtex.

On completion of the run after 300 h, the left-over yarn, which remained intact in its yarn structure, was washed with hot water and then dried.

No viscose fiber was detectable microscopically or chemically.

As the analysis showed, the left-over portion consisted of pure polyester fibers which are easy to recycle.

What is claimed is:

1. A process for recycling materials containing cellulose fiber mixtures comprising the steps of:

i) providing a mixture of cellulose and polyester fibers, ii) subjecting the mixture to a hydrolysis in which the cellulosic fibers are degraded by contacting the fibers with microorganisms to form a hydrolyzate, iii) removing the microorganisms and hydrolyzate, and iv) fermenting the hydrolyzate anaerobically to form a methane-containing gas.

2. The process of claim 1 wherein the mixtures used comprise a) fiber mixtures comprising cellulosic fibers and fibers composed of synthetic polymers and b) further microbially hydrolyzable constituents.

3. The process of claim 1 wherein the microbial hydrolysis and the anaerobic fermentation are carried out together as one process step.

* * * * *